United States Patent
Shipley et al.

(10) Patent No.: US 8,147,135 B2
(45) Date of Patent: Apr. 3, 2012

(54) METHODS AND SYSTEMS FOR VERIFYING SENSOR BOND INTEGRITY

(75) Inventors: John L. Shipley, Tremonton, UT (US); Jerry W. Jenson, Thatcher, UT (US); Mark R. Eggett, Brigham City, UT (US)

(73) Assignee: Alliant Techsystems Inc., Arlington, VA (US)

( * ) Notice: Subject to any disclaimer, the term of this patent is extended or adjusted under 35 U.S.C. 154(b) by 844 days.

(21) Appl. No.: 12/046,553

(22) Filed: Mar. 12, 2008

(65) Prior Publication Data

US 2009/0229372 A1 Sep. 17, 2009

(51) Int. Cl.
*G01N 25/00* (2006.01)
*G01N 17/00* (2006.01)

(52) U.S. Cl. .............................. 374/57; 374/7
(58) Field of Classification Search ............ 374/57, 374/7

See application file for complete search history.

(56) References Cited

U.S. PATENT DOCUMENTS

| | | | |
|---|---|---|---|
| 4,442,718 A | 4/1984 | Komarova et al. | |
| 4,831,258 A * | 5/1989 | Paulk et al. | 250/349 |
| 5,651,284 A | 7/1997 | Leon | |
| 5,709,469 A | 1/1998 | White et al. | |
| 5,841,034 A | 11/1998 | Ball | |
| 6,026,881 A * | 2/2000 | Durso | 156/359 |
| 6,301,971 B1 | 10/2001 | Sykes | |
| 6,490,047 B2 | 12/2002 | Siu | |
| 6,565,686 B2 * | 5/2003 | Bett et al. | 156/64 |
| 6,951,137 B2 | 10/2005 | Smith et al. | |
| 7,041,960 B2 | 5/2006 | Sato | |
| 7,077,011 B2 | 7/2006 | Johnson et al. | |
| 7,425,093 B2 * | 9/2008 | Wickersham et al. | 374/5 |
| 7,461,560 B2 | 12/2008 | Arms et al. | |
| 2004/0218660 A1 * | 11/2004 | Heerdt et al. | 374/129 |
| 2005/0169346 A1 * | 8/2005 | Murray et al. | 374/121 |
| 2006/0009865 A1 | 1/2006 | Goldfine et al. | |
| 2009/0168074 A1 * | 7/2009 | Monchalin et al. | 356/502 |

* cited by examiner

*Primary Examiner* — Lisa Caputo
*Assistant Examiner* — Mirellys Jagan
(74) *Attorney, Agent, or Firm* — TraskBritt

(57) ABSTRACT

Methods and systems are disclosed for determining an amount of bond between a structure and sensor. A method may include heating a sensor that is operably coupled to a measuring circuit and then measuring an output signal over time. The method may further include determining, from the output signal, a percentage of bond integrity remaining between the sensor and the structure. A system may include a measurement circuit having a sensor operably coupled to a sensing system. The sensing system may be configured for applying a thermal shock to the sensor and subsequently measuring an output signal of the measuring circuit. The sensing system may also be configured for determining, from the output signal, an amount of bond between the sensor and the structure.

25 Claims, 6 Drawing Sheets

METHODS AND SYSTEMS FOR VERIFYING SENSOR BOND INTEGRITY

CROSS-REFERENCE TO RELATED APPLICATIONS

This application is related to copending U.S. patent application Ser. No. 12/631,600, entitled "Methods and Systems for Verifying Sensor Bond Integrity and Structures Employing such Systems," filed Dec. 4, 2009, which is a continuation-in-part of this application.

TECHNICAL FIELD

This invention, in various embodiments, relates generally to sensors configured to measure a physical property and, more specifically, methods and systems for verifying the integrity of a bond between a sensor and a structure on which a physical property is to be measured.

BACKGROUND OF THE INVENTION

A strain gauge is a strain-sensitive resistive device employed to sense strain, such as that caused by stress in the form of tensile or compressive forces applied to a structure. Conventional strain gauges typically employ a strain sensing element adhered to a surface of the structure such that, when the structure exhibits a strain in response to an applied stress, the resistance of the sensing element changes in proportion to the sensed strain. The measured strain is generally calculated based on the change in resistance in the sensing element as the structure is compressed or elongated, thus exhibiting or manifesting the strain. Strain gauges can be used to measure bending, axial and torsional or a combination of strain effects on a structure resulting from various applied loads.

Strain gauges may include foil type strain gauges comprising a pattern of resistive foil mounted on a backing surface. Furthermore, strain gauges may include semiconductor strain gauges which are often preferred over foil gauges when measuring small amounts of strain. Strain gauges are usually attached to a flexible plastic substrate which, in turn, is bonded to the structure for which the strain is to be determined.

A sensing element for a strain gauge is conventionally implemented within a Wheatstone bridge circuit which converts the sensed resistance to a voltage signal. To obtain the voltage signal, it is generally required to further connect a differential amplifier and a current source to the Wheatstone bridge circuit. FIG. 1 is a schematic diagram of Wheatstone bridge circuit 100 including four branches, one of which may include a resistive transducer, such as a strain gauge 110. The other branches of Wheatstone bridge circuit 100 include resistors $R_1$, $R_2$, and $R_3$, each with resistances equal to that of the strain gauge 110. An input DC voltage, or excitation voltage $V_{in}$, is applied between the top and bottom of circuit 100 and an output voltage $V_{out}$ is measured across the middle of circuit 100. When the output voltage is zero, circuit 100 is balanced. As the resistance of one of the branches changes, by a strain of a resistive strain gauge for example, the previously balanced circuit becomes unbalanced. This unbalance causes a voltage $V_{out}$ to appear across the middle of circuit 100. This induced voltage may be measured with a voltmeter or the resistor $R_3$ in the opposite branch may be adjusted to rebalance circuit 100. In either case, the change in resistance that caused the induced voltage may be measured and converted to obtain a degree of strain.

FIG. 2 illustrates a conventional strain sensing system 200. System 200 includes a strain sensor 210 in electrical communication with a sensing system 220. Strain sensor 210 may include circuitry, such as the Wheatstone bridge circuit 100 shown in FIG. 1. Furthermore, strain sensor 210 may be coupled to a structure for sensing strain responsive to stress experienced by the structure due to an applied force or forces. Strain sensor 210 produces an electrical signal that is used by the sensing system 220 for identifying the strain force on the object and presenting the identified force to an observer.

The accuracy of data reported by a sensor, such as a strain gauge, mounted to a structure depends to a high degree on the integrity of the adhesive bond between the sensor and the structure. It is generally accepted that the adhesive bond (e.g., an epoxy) may break down or debond over time due to various conditions, such as fatigue or corrosion due to exposure to elements, such as moisture. A sensor which is debonded even slightly may result in failure or malfunction of the sensor and may, at best, provide incorrect strain measurements. Furthermore, conventional sensors do not always provide sufficient warning of potential gauge failure or malfunction.

The bond between a sensor and a structure of interest is conventionally inspected by visual or tactile means which are time consuming and often inconclusive. Furthermore, a sensor may reside in a location not accessible to a human inspector.

There is a need to enhance the efficiency and reliability of measuring a physical property on a structure of interest. Specifically, there is a need for methods, devices, and systems for verifying the integrity of a bond between a sensor for measuring a physical property of a structure and the structure of interest.

BRIEF SUMMARY OF THE INVENTION

An embodiment of the present invention comprises a method of determining bond integrity between a sensor and a structure. The method comprises heating a sensor bonded to a structure of interest and operably coupled to a measuring circuit during a sufficiently short time period to leave the structure in a substantially unheated state and measuring an output signal of the measuring circuit. The method further includes determining an amount of bond integrity between the sensor and an adjacent structure based on the output signal.

Another embodiment of the present invention includes a system comprising a sensor operably coupled to a measuring circuit and a sensing system operably coupled to the measuring circuit. Furthermore, the sensing system is configured for selectively applying a thermal shock to the sensor and measuring an output signal of the measuring circuit. Additionally, the sensing system is configured for determining an amount of bond integrity between the sensor and an adjacent structure of interest to which the sensor may be bonded based on the output signal.

Yet another embodiment of the present invention includes a method of determining bond integrity between a sensor and an adjacent structure to which the sensor is bonded. The method comprises heating a sensor during a time period sufficiently short to leave the adjacent structure in a substantially unheated state and monitoring a physical parameter of the sensor. Furthermore, the method includes determining an amount of bond integrity between the sensor and the adjacent structure based on the physical parameter.

DETAILED DESCRIPTION OF THE INVENTION

The present invention, in various embodiments, comprises apparatuses and methods of verifying the integrity of a bond between a structure and a sensor attached thereto. In the following description, circuits and functions may be shown in block diagram form in order not to obscure the present invention in unnecessary detail. Conversely, specific circuit implementations shown and described are examples only and should not be construed as the only way to implement the present invention unless specified otherwise herein. Additionally, block definitions and partitioning of logic between various blocks is exemplary of a specific implementation. It will be readily apparent to one of ordinary skill in the art that the present invention may be practiced by numerous other partitioning solutions. For the most part, details concerning timing considerations and the like have been omitted where such details are not necessary to obtain a complete understanding of the present invention and are within the abilities of persons of ordinary skill in the relevant art.

In this description, some drawings may illustrate signals as a single signal for clarity of presentation and description. It will be understood by a person of ordinary skill in the art that the signal may represent a bus of signals, wherein the bus may have a variety of bit widths and the present invention may be implemented on any number of data signals, including a single data signal. In describing embodiments of the present invention, the systems and elements incorporating embodiments of the invention are described to facilitate an enhanced understanding of the function of the described embodiments of the invention as it may be implemented within these systems and elements.

As known by one having ordinary skill in the art, a sensor, such as a transducer may be configured to convert a physical property (e.g., temperature, light, magnetic field, strain, acceleration, sound intensity) to an electrical property, such as voltage, resistance, or current. Furthermore, as is well known in the art, a sensor may be attached to a structure and may be used to determine a physical property on the structure. As described above a strain gauge sensor conventionally employs a strain sensing element adhered to a surface of a structure such that when the structure exhibits a strain, the resistance of the sensing element changes in proportion to the sensed strain. A resistance temperature detector (RTD) sensor also employs a sensing element to provided a change in resistance proportional to a change in temperature of the structure to which the RTD is attached. As such, RTDs and strain gauges produce small changes in resistance in response to a change in a physical property such as temperature or strain. For example only, and not by way of limitation, a strain gauge may be attached to a pressure vessel, such as a rocket motor, and used to determine an amount of strain exhibited by the pressure vessel.

Figure 1:
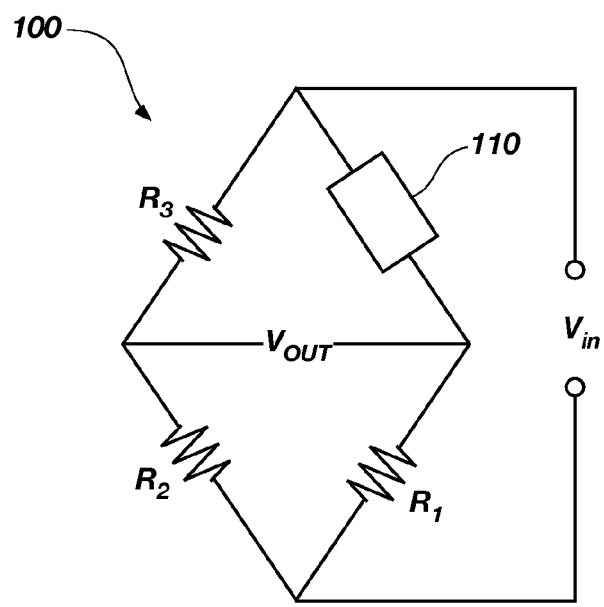
FIG. 1 is a schematic diagram of a Wheatstone bridge circuit incorporating a strain gauge.
Figure 2:
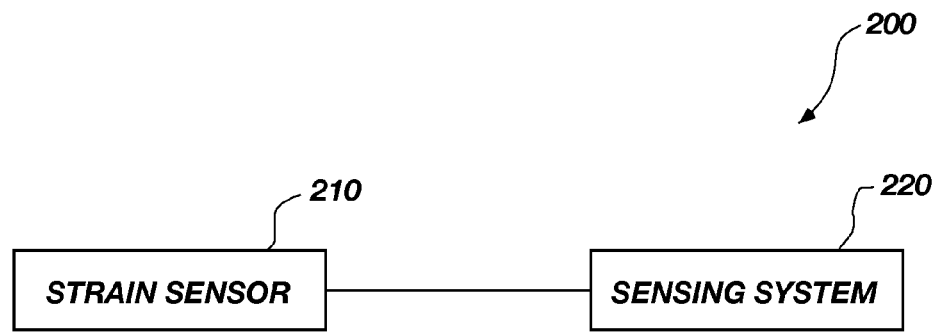
FIG. 2 is a conventional strain sensing system including a strain sensor in electrical communication with a sensing system.
Figure 3:
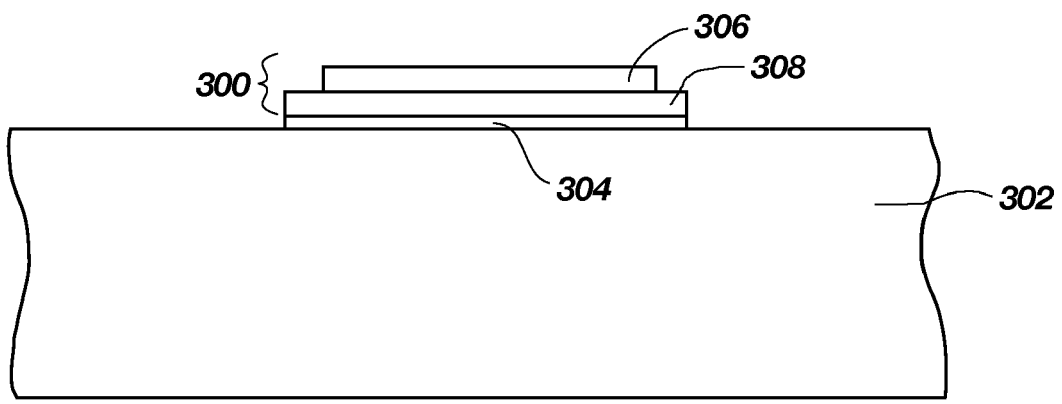
FIG. 3 is a cross-sectional diagram of a sensor bonded to a structure.

FIG. 3 illustrates a sensor 300 attached to a structure 302. For explanation purposes only, sensor 300 may comprise a strain gauge. As a non-limiting example, sensor 300 may include a constantan foil 306 plated on a polyimide layer 308. Sensor 300 may be positioned and affixed to structure 302 by attaching or fastening sensor 300 using an appropriate fastening technique. Such a fastening technique may include bonding sensor 300 to structure 302 using a suitable bonding agent 304, for example, such as an epoxy or other adhesive. As explained above, it is possible for a sensor to debond from a structure for various reasons, such as fatigue or corrosion. The accuracy of the information provided by sensor 300 may depend to a high degree on the integrity of bond between sensor 300 and structure 302. Accordingly, at some level of bonding degradation, the information provided by sensor 300 may not be trustworthy.

An example of a method of determining the integrity of a bond between a sensor and a test structure will first be described in general. Subsequently, a more detailed example with reference of FIGS. 4A and 4B will be provided. Thereafter, output results of tests performed on a sensor will be described in reference to FIGS. 5-8.

Initially, a sensor, adjacent to a structure, may be heated in a quick manner by any means known in the art so as to heat the sensor without beating the structure to any substantial or detectable extent. For example only, heating a sensor may comprise applying a thermal shock for a short duration to the sensor by any method known in the art, such as photo flash heating, electrical heating, or external heating. Photo flash heating may comprise utilizing a flash lamp, as known in the art, and directing it toward the sensor. Furthermore, the sensor may be heated by an external device such as a blower or hair dryer. In addition, as described more fully below, the sensor may be electrically heated by applying an increased current or an increased voltage to the sensor. Accordingly, after applying a thermal shock, the sensor will register a shift in temperature that will decay over time. Based on the general principles of heat transfer, it will be understood by one having ordinary skill in the art that if the sensor is at least partially debonded from a structure, the temperature of the sensor will increase a greater amount than it would if the sensor was fully bonded to the structure. After heating a sensor, the shift in a physical property, such as temperature or strain, and the rate of decay of the shift may be measured over time resulting in measured data. Thereafter, the measured data may be compared to reference data in order to determine an amount of bond (e.g., a percentage of bond) remaining between a sensor and a structure. Stated another way, the bond integrity between a sensor and a structure of interest to which the sensor is affixed may be characterized in terms of percent of an initial, known bond integrity. Reference data may include voltage, temperature or strain measurements taken from a test sensor with a known amount of bond between the test sensor and a test structure. For example, the measured data may be compared against reference data obtained from tests performed on a model sensor. Furthermore, the reference data may, for example only include data obtained from earlier tests performed on the same sensor. Furthermore, for example only, the measured data may be compared against reference data obtained by computational methods if the material properties of a test sensor and test structure are known.

Figure 4A:
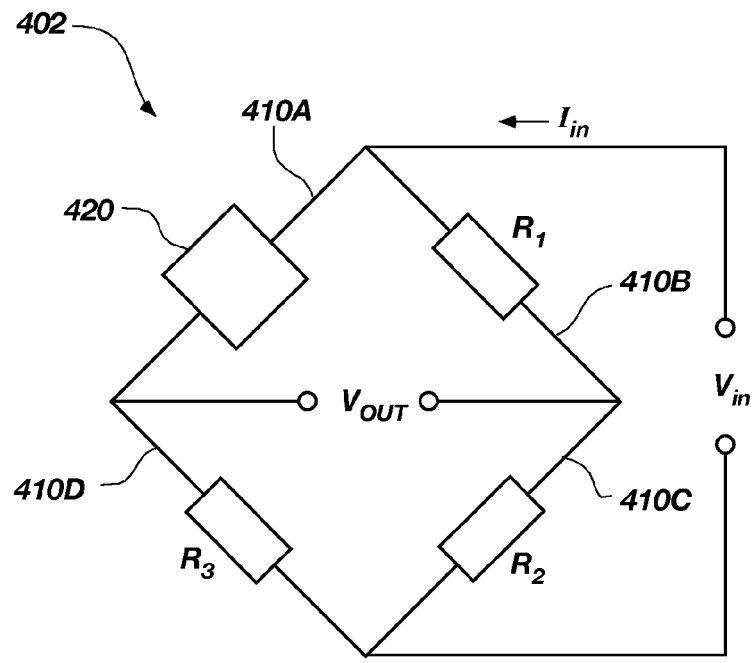
FIG. 4A illustrates a sensor within a measurement circuit suitable for use in accordance with an embodiment of the invention.

A more detailed example of determining the amount or percentage of a bond between a sensor and a structure will now be described. As known by one having ordinary skill in the art, in order to measure a physical property with a bonded sensor, the sensor may be integrated within a measurement circuit configured to measure the changes in an electrical property corresponding to a change in a physical property, such as temperature or strain. For example only, a measurement circuit may include a Wheatstone bridge circuit including at least one sensor configured to measure electrical resistance. FIG. 4A illustrates an example of a Wheatstone bridge circuit 402 having four branches 410A, 410B, 410C, and 410D. Branch 410A may include a sensor 420, and branches 410B, 410C, and 410D may include resistors $R_1$, $R_2$, and $R_3$, respectively. Although Wheatstone bridge circuit 402, as shown in FIG. 4A, includes sensor 420 located within branch 410A, a Wheatstone bridge may take various forms. For example, sensor 420 may be located within branch 410B, 410C, or 410D. Furthermore, although Wheatstone bridge circuit 402 is illustrated as a "quarter" Wheatstone bridge (i.e., only one of the four branches includes a sensor), embodiments of the invention may be applicable to full bridges (i.e., having a sensor within each branch) and half bridges (i.e., two of the four branches include a sensor). For example only, and not by way of limitation, sensor 420 may comprise an RTD or a strain gauge.

Figure 4B:
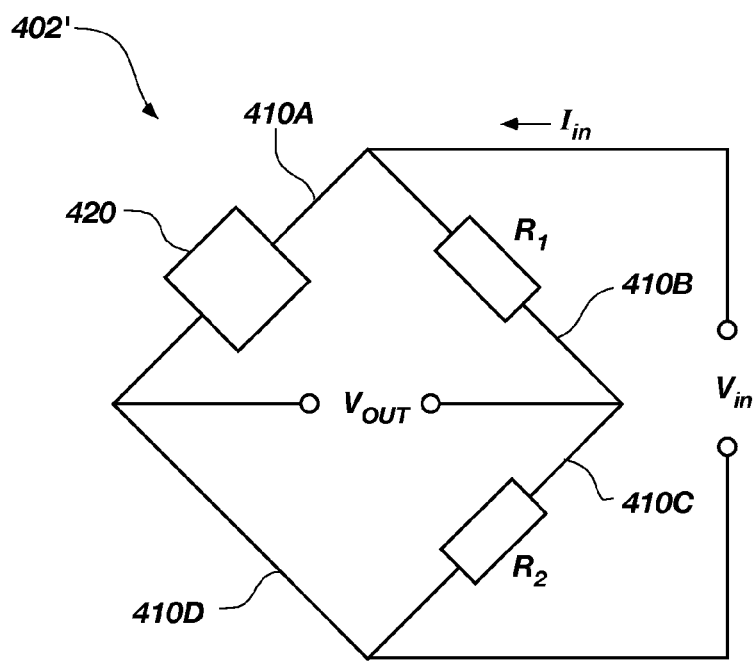
FIG. 4B illustrates the sensor within the measurement circuit of FIG. 4A during application of heat, in accordance with an embodiment of the invention.

Referring to FIGS. 4A and 4B, initially, a thermal shock may be applied to sensor 420 by way of electrical heating. Although the following description discusses applying a thermal shock by way of electrical heating, embodiments of the present invention are not so limited and any method known in the art and suitable for applying a thermal shock to a given sensor in a particular environment is within the scope of the invention. According to one embodiment of the present invention, a thermal shock may be applied to sensor 420 by first supplying a current $I_{in}$ and an input voltage $V_{in}$ to Wheatstone bridge circuit 402. Subsequently, resistor $R_3$, which is in series with sensor 420, may be shorted out, resulting in circuit 402', as shown in FIG. 4B. With resistor $R_3$ shorted out, a voltage across sensor 420 may be approximately doubled due to the entire input voltage $V_{in}$ being applied across sensor 420. As a result, a temperature of sensor 420 may be increased. The application of heat may then be eliminated by removing the short (resulting, again, in circuit 402 illustrated in FIG. 4A) and an output signal, such as voltage $V_{out}$, may be monitored as sensor 420 returns to the pre-thermal shock condition. By methods known in the art, a resistive response and a temperature response of sensor 420 over time may be determined from the response of output voltage $V_{out}$ over time.

Referring again to FIG. 4A, and according to another embodiment of the present invention, a thermal shock may be applied to sensor 420 by supplying an increased voltage (i.e., a voltage greater than $V_{in}$) to Wheatstone bridge circuit 402 for a short period of time (e.g., 0.13 seconds). As a result, the temperature of sensor 420 may be increased. Subsequently, the application of heat may be terminated by decreasing the voltage to $V_{in}$. At anytime during the application of heat, or after the application of heat is terminated, a resistive or a temperature response of sensor 420 over time may be monitored as sensor 420 returns to the pre-thermal shock condition.

According to yet another embodiment, a thermal shock may be applied to sensor 420 by supplying an increased current (i.e., a current greater than current $I_{in}$) to Wheatstone bridge circuit 402 for a short period of time and, therefore increasing the temperature of sensor 420. Subsequently, the application of heat may be terminated by decreasing the current to current $I_{in}$. At anytime during the application of heat, or after the application of heat is terminated, a resistive or a temperature response of sensor 420 over time may be monitored as sensor 420 returns to the pre-thermal shock condition.

As mentioned above, embodiments of the invention are not limited to quarter Wheatstone bridge circuits but, rather, embodiments of the present invention may be implemented with full or half Wheatstone bridge circuits. As understood by one having ordinary skill in the art, each sensor within a full or half Wheatstone bridge circuit may be individually tested by heating a specific sensor by applying short circuits and/or injecting voltages at appropriate locations within the circuit and monitoring a resistive or temperature response of the sensor during a time period while heating the sensor, during a time period after terminating the application of heat to the sensor, or any combinations thereof.

FIGS. 5-8 illustrate results obtained from tests done on a strain gauge according to various bonding percentages between the strain gauge and a structure. In these tests, the strain gauge was heated, for example, for approximately 0.13 seconds and the output results (i.e., temperature or strain) were monitored with respect to time.

Figure 5:
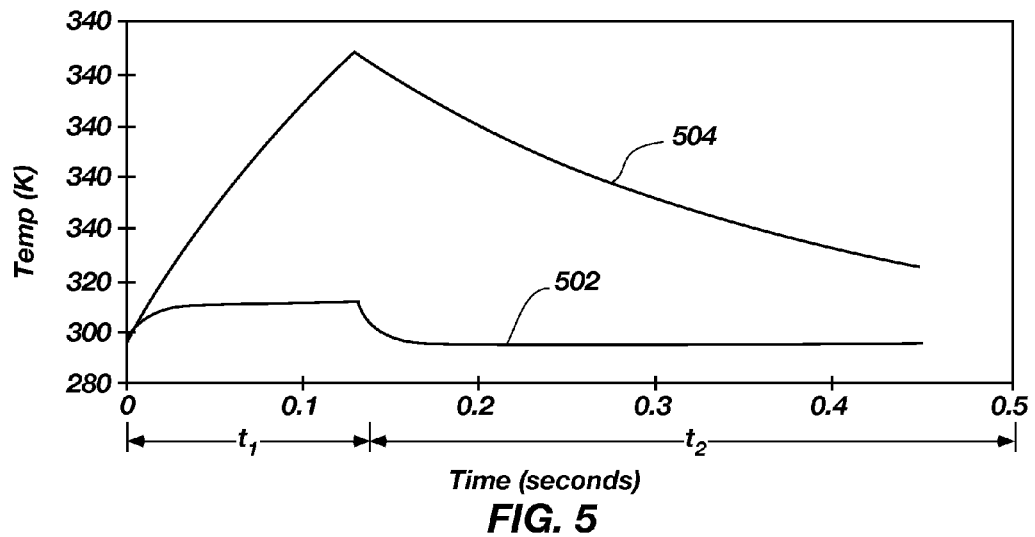
FIG. 5 is a plot illustrating a temperature versus time relationship of a fully bonded sensor and a fully unbonded sensor after application of heat to each sensor.

FIG. 5 is a plot illustrating a comparison of the change of temperature over time for a fully bonded strain gauge and a fully unbonded strain gauge during a first time period $t_1$ wherein heat is applied to the strain gauge, and a second time period $t_2$ immediately following removal of the heat. As shown in FIG. 5, the temperature of a fully unbonded strain gauge (signal 504) quickly increases from approximately 300 Kelvin to above 400 Kelvin during the first time period $t_1$. Subsequently, after ceasing the application of heat the temperature of the fully unbonded strain gauge decreases toward its original state during time period $t_2$. On the other hand, the temperature of a fully bonded strain gauge (signal 502) increases from approximately 300 Kelvin to approximately 310 Kelvin during the first time period $t_1$. Subsequently after ceasing the application of heat, the temperature of the fully bonded strain gauge decreases to its original state during time period $t_2$.

Figure 6:
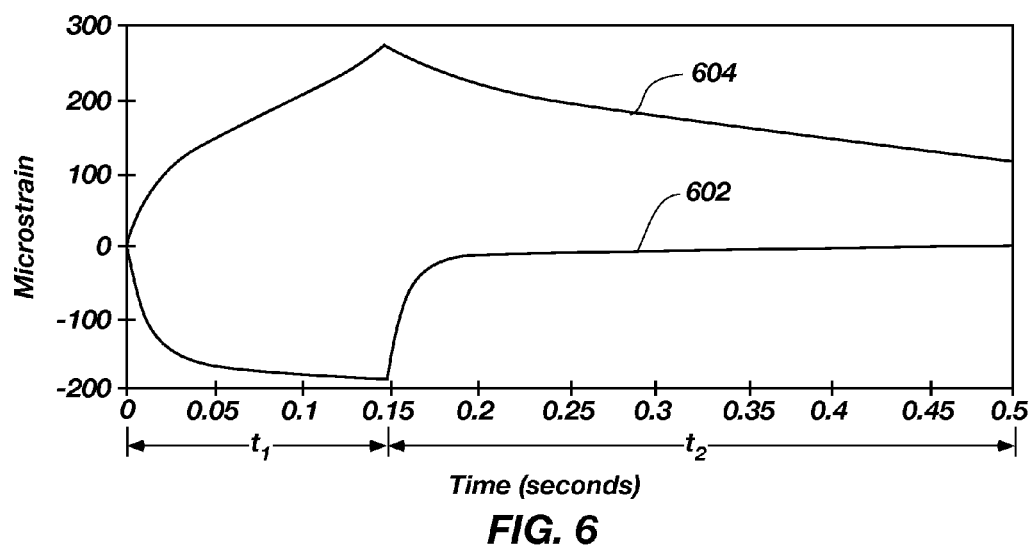
FIG. 6 is a plot illustrating a strain versus time relationship of a fully bonded sensor and a fully unbonded sensor after application of heat to each sensor.

FIG. 6 is a plot illustrating a comparison of the change of strain over time of a fully bonded strain gauge and a fully unbonded strain gauge during a first time period $t_1$ wherein heat is applied to the strain gauge, and a second time period $t_2$ immediately following removal of the heat. As shown in FIG. 6, a fully bonded strain gauge (signal 602) exhibits a decrease in strain during application of heat (i.e., during time period $t_1$). This decrease in strain is due to the fact that a fully bonded strain gauge is constrained form expansion during the application of heat because of the fully bonded configuration. As a result, the fully bonded strain gauge compresses and the strain measured by the strain gauge decreases. After removing the heat, the strain of the fully bonded strain gauge increases to its original state during time period $t_2$. On the other hand, a fully unbonded strain gauge (signal 604) exhibits an increase in strain during application of heat (i.e., during time period $t_1$). This increase in strain is due to fact that a fully unbonded strain gauge is unconstrained and, therefor, expands during the application of heat (i.e., during time period $t_1$). As a result, the strain of the fully unbonded strain gauge increases. After removing the heat, the strain of the fully unbonded strain gauge decreases toward its original state during time period $t_2$.

Figure 7:
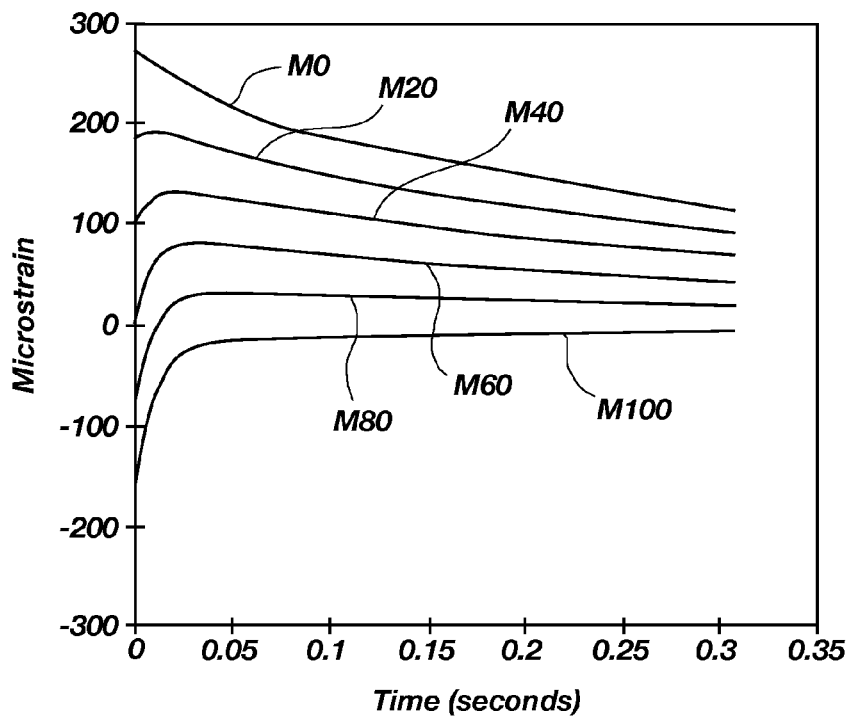
FIG. 7 is a plot of model data illustrating a strain versus time relationship of a model sensor according to various bonding percentages.

FIG. 7 is a plot illustrating reference data including strain signals generated from a model sensor having various bonding percentages between the model sensor and a model test structure. Furthermore, the time period illustrated in FIG. 7 represents a time period immediately following removal of heat to the model sensor. Signals M100, M80, M60, M40, M20, and M0 represent strain signals generated from a model sensor respectively having a 100%, 80%, 60%, 40%, 20%, and 0% bond to a model test structure.

Figure 8:
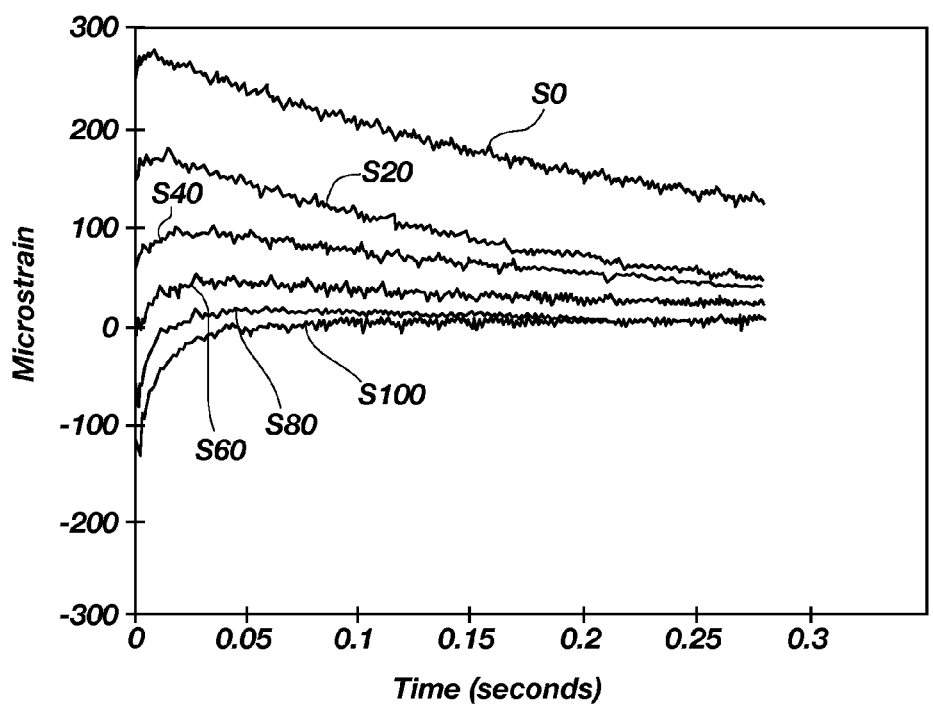
FIG. 8 is a plot of actual measured data illustrating a strain versus time relationship of a sensor according to various bonding percentages.

FIG. 8 is a plot illustrating measured data including strain signals generated from a sensor with various bonding percentages between the sensor and a structure. During an initial test, with the sensor fully bonded (i.e., 100%), the sensor was subjected to a thermal shock during a first time period and an output voltage was monitored over a second time period. Subsequently, a strain measurement was calculated for the second time period resulting in output signal S100. Thereafter, the sensor was peeled from the structure creating a bond of approximately 80%, which when subjected to a thermal shock, produced an output signal S80. Similarly, in successive tests, the sensor was peeled away from the test structure creating bonds of approximately 60%, 40%, 20%, and 0%, which correlate to output signals S60, S40, S20, and S0, respectively.

As mentioned above, reference data, generated from, for example, tests performed on a model sensor or computational methods, may be compared with the measured data (i.e., the shift in temperature or strain and rate of decay of the temperature or strain over time) in order to quantify the percentage of bond existing between the sensor and the structure. For example, the measured data illustrated in FIG. 8 may be compared against the model data illustrated in FIG. 7 in order to approximate an amount of bond between a sensor and a structure.

Although the examples described below include sensors implemented with a Wheatstone bridge circuit, embodiments of the present invention are not so limited, and embodiments of the present invention may include sensors implemented by any acceptable measurement circuit configuration as known by one having ordinary skill in the art. Furthermore, although embodiments of the invention have been described in reference to strain gauge sensors or resistance temperature detector sensors, embodiments of the invention may be applicable to any sensor that may be bonded to a test structure. Embodiments of the disclosure may also be applicable to internal structures, such as pressure gages and accelerometers.

Figure 9:
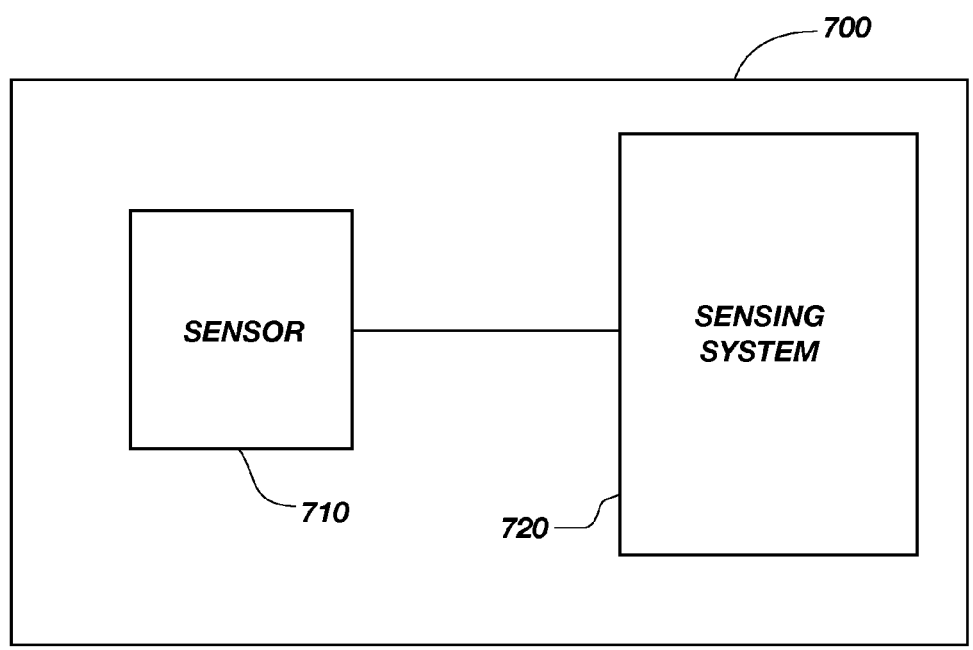
FIG. 9 is a block diagram of a system including a sensor and sensing system, according to an embodiment of the invention.

FIG. 9 illustrates a system 700 including a sensor 710 configured to sense a physical property of a structure attached thereto. Physical properties sensed by sensor 710 may include, for example only, temperature, light, magnetic field, strain, acceleration, or sound intensity. As a nonlimiting example, sensor 710 may include a strain gauge or an RTD, as described above. Furthermore, system 700 may be configured as an automated sensing system 720 configured to periodically verify a bond integrity between a structure 302 (see FIG. 3) and sensor 710 attached thereto. Sensing system 720 may be adapted to apply an input voltage and an input current to sensor 710. Furthermore, sensing system 720 may be configured to apply heat to sensor 710 for a short period of time, to remove the heat, and to subsequently receive an output signal from sensor 710. Sensing system 720 may further be configured to monitor the output signal over time, generate measured data (e.g., a physical property, such as temperature or strain) over time, compare the measured data to known reference data, and quantify an amount of bond between sensor 710 and structure 302.

Specific embodiments have been shown by way of example in the drawings and have been described in detail herein; however, the invention may be susceptible to various modifications and alternative forms. It should be understood that the invention is not intended to be limited to the particular forms disclosed. Rather, the invention includes all modifications, equivalents, and alternatives falling within the scope of the invention as defined by the following appended claims, and their legal equivalents.

What is claimed is:

1. A method of measuring bond integrity between a sensor and a structure, comprising:
heating a sensor bonded to a structure of interest and operably coupled to a measuring circuit during a sufficiently short time period to leave the structure of interest in a substantially unheated state;
monitoring an output signal of the measuring circuit responsive to the heating of the sensor; and
determining an amount of bond between the sensor and the structure of interest based on the output signal.

2. The method of claim 1, wherein heating a sensor comprises heating the sensor with at least one of a heated blower and a flash lamp.

3. The method of claim 1, wherein monitoring an output signal of the measuring circuit comprises monitoring an output signal of the measuring circuit subsequent to heating the sensor.

4. The method of claim 1, wherein heating a sensor comprises heating at least one of a strain gauge and a resistive temperature detector.

5. The method of claim 1, wherein heating a sensor operably coupled to the measuring circuit comprises heating a sensor operably coupled to a Wheatstone bridge circuit.

6. The method of claim 1, further comprising calculating an amount of strain measured by the sensor from the output signal.

7. The method of claim 6, wherein determining an amount of bond between the sensor and the structure of interest comprises comparing the amount of strain measured by the sensor to at least one reference data strain measurement.

8. The method of claim 1, further comprising calculating a temperature measured by the sensor from the output signal.

9. The method of claim 8, wherein determining an amount of bond between the sensor and the structure of interest comprises comparing the temperature measured by the sensor to at least one reference data temperature measurement.

10. The method of claim 1, wherein heating a sensor comprises electrically heating the sensor.

11. The method of claim 10, wherein electrically heating the sensor comprises at least one of increasing a voltage applied to the sensor and increasing a current applied to the sensor.

12. A system, comprising:
a sensor operably coupled to a measuring circuit; and
a sensing system, wherein the sensing system is configured for:
selectively applying a thermal shock to the sensor;
measuring an output voltage of the measuring circuit responsive to the thermal shock; and determining a percentage of bond between the sensor and an adjacent structure to which the sensor is affixed based on the measured output voltage.

13. The system of claim 12, wherein applying a thermal shock to the sensor comprises heating the sensor with at least one of a heated blower and a flash lamp.

14. The system of claim 12, wherein measuring an output voltage of the measuring circuit comprises measuring an output voltage of the measuring circuit during a time period subsequent to application of the thermal shock.

15. The system of claim 12, wherein applying a thermal shock to the sensor comprises applying a thermal shock to at least one of a strain gauge and a resistive temperature detector operably coupled to the measuring circuit.

16. The system of claim 12, wherein applying a thermal shock to the sensor operably coupled to the measuring circuit comprises applying a thermal shock to the sensor operably coupled to a Wheatstone bridge circuit.

17. The system of claim 12, wherein the sensing system is further configured for determining a amount of strain measured by the sensor from the output voltage.

18. The system of claim 17, wherein determining a percentage of bond between the sensor and a test structure comprises comparing the amount of strain to at least one reference data strain measurement.

19. The system of claim 12, wherein the sensing system is further configured for determining a temperature measured by the sensor from the output voltage.

20. The system of claim 19, wherein determining a percentage of bond between the sensor and a test structure comprises comparing the temperature measured by the sensor to at least one reference data temperature measurement.

21. The system of claim 12, wherein applying a thermal shock to the sensor comprises electrically heating the sensor.

22. The system of claim 21, wherein electrically heating the sensor comprises at least one of increasing a voltage applied to the sensor and increasing a current applied to the sensor.

23. A method of determining an amount of bond between a sensor and a structure, comprising:
  applying heat to a sensor bonded to a structure of interest during a time period sufficiently short to leave the structure of interest in a substantially unheated state;
  monitoring a physical parameter of the sensor to generate data responsive to the application of heat to the sensor; and
  determining an amount of bond between the sensor and a structure adjacent thereto based on the generated data.

24. The method of claim 23, wherein monitoring a physical parameter of the sensor comprises monitoring one of a strain measured by the sensor and a temperature measured by the sensor.

25. The method of claim 23, wherein determining an amount of bond comprises comparing the generated data with reference data.

* * * * *

UNITED STATES PATENT AND TRADEMARK OFFICE
CERTIFICATE OF CORRECTION

PATENT NO.        : 8,147,135 B2  
APPLICATION NO.   : 12/046553  
DATED             : April 3, 2012  
INVENTOR(S)       : Shipley et al.

Page 1 of 1

It is certified that error appears in the above-identified patent and that said Letters Patent is hereby corrected as shown below:

In the claims:
CLAIM 17, COLUMN 9, LINE 20, change "a amount" to --an amount--

Signed and Sealed this
Twenty-eighth Day of January, 2014

Michelle K. Lee
*Deputy Director of the United States Patent and Trademark Office*